(12) United States Patent
Wang et al.

(10) Patent No.: US 6,683,975 B2
(45) Date of Patent: Jan. 27, 2004

(54) APPARATUS AND METHOD FOR DETERMINING THE DISPERSIBILITY OF A PRODUCT IN PARTICULATE FORM

(75) Inventors: Jianjun Wang, Dublin, OH (US); Randall Edwin Terflinger, Pickerington, OH (US); Wilson G. Zeitler, Westerville, OH (US); David A. Mondiek, Dublin, OH (US)

(73) Assignee: Abbott Laboratories, Abbott Park, IL (US)

( * ) Notice: Subject to any disclaimer, the term of this patent is extended or adjusted under 35 U.S.C. 154(b) by 79 days.

(21) Appl. No.: 09/883,715

(22) Filed: Jun. 18, 2001

(65) Prior Publication Data

US 2003/0016857 A1 Jan. 23, 2003

(51) Int. Cl.[7] .................................................. G06K 9/00
(52) U.S. Cl. ....................................................... 382/141
(58) Field of Search ................................ 382/141, 142, 382/192, 204, 209, 218

(56) References Cited

U.S. PATENT DOCUMENTS

| | | | | |
|---|---|---|---|---|
| 5,436,980 A | * | 7/1995 | Weeks et al. | 382/141 |
| 5,880,830 A | * | 3/1999 | Schechter | 356/318 |

FOREIGN PATENT DOCUMENTS

| | | | | |
|---|---|---|---|---|
| WO | 98/30886 A1 | 7/1998 | | G01N/15/02 |

OTHER PUBLICATIONS

PCT Search Report, PCT/US02/17566.
Standard Test Method for Bulk Solids Characterization by Carr Indices[1], American Society For Testing and Materials, D 6393–99.
Do All Soy Formulas Shake Out? Powder Mixability Varies Greatly Among Soy Formulas, Ross Laboratories, Columbus, Ohio, 1987.

(List continued on next page.)

Primary Examiner—Brian Werner
(74) Attorney, Agent, or Firm—David I. Weinstein (57) ABSTRACT

A method and apparatus for determining the dispersibility grade of particulate material by means of an image processing technique that employs machine vision. In one aspect, this invention provides a method for grading the dispersibility of particulate material, the method comprising the steps of:

(a) obtaining an image, in digitized form, of a sample comprising reconstituted particulate material;
(b) performing a series of image processing steps to determine the presence and magnitude of blobs;
(c) performing a blob analysis to obtain data relating to the distribution of the particulate material in the sample;
(d) comparing the result of the blob analysis with data in a database; and
(e) determining the grade of said particulate material by means of the comparison.

The sample of particulate material, which is typically in the form of a powder, is reconstituted preferably by means of agitating a container filled with the sample.

The database suitable for use in this invention can be established by recording the results of a large number of tests performed by a powder quality grading authority. The grade levels are associated with several ranges that have emerged from the statistical analysis. In another aspect, this invention provides an apparatus suitable for grading the dispersibility of particulate material.

17 Claims, 10 Drawing Sheets

OTHER PUBLICATIONS

Robert Gregory, "Planning a PC–Based Machine Vision System", Sensors, Apr. 1998, pp. 12–18.

E.J. Claude and R.M. Carrite, "Increasing Product Yields with Automated Visions Systems", Medical Device & Diagnostic Industry, May 2000, pp. 158–169.

E.R. Davies, *Machine Vision: Theory, Algorithms, Practicalities*, $2^{nd}$ Edition, Academic Press (1997), pp. 19–39, 79–130, 245–269, 348–371, 471–528, 561–601, 603–620, 677–695.

* cited by examiner

APPARATUS AND METHOD FOR DETERMINING THE DISPERSIBILITY OF A PRODUCT IN PARTICULATE FORM

BACKGROUND OF THE INVENTION

1. Field of the Invention

This invention relates to the field of machine vision, and, more particularly, the use of machine vision to determine the dispersibility grade of a product in particulate form.

2. Discussion of the Art

Infant formula powder manufacturers have used dispersibility to describe the degree of firmness and solubility of particulate materials within a product. Such particulate materials include, for example, gel, mineral, and oil. These particulate materials may cause coagulation of the product or sedimentation in the product, both of which are not desired.

The conventional procedure for determining dispersibility comprises the following steps:

(a) providing a quantity of particulate material, e.g., infant formula powder, for each sample to be tested;

(b) introducing a quantity of tap water at a specified temperature into a container;

(c) applying the quantity of particulate material to the surface of the water and placing a cover on the container;

(d) agitating the container in such a manner, e.g., on a mechanical shaker, to disperse the particulate material to form a dispersion;

(e) pouring the dispersion through an 80 mesh screen;

(f) filling the container approximately ¼ full with tap water to dislodge any particulate material that may remain in the container, and pouring the resultant dispersion through the screen; and (g) rating the particulate material remaining on the screen by referring to a series of standard photographs of samples of differing grades.

Each sample is tested in duplicate and the average reported as the final result.

This test and similar tests are performed manually. The results are highly dependent on the personal experience of the evaluator and are subject to deviation from evaluator to evaluator, location to location, or even day to day. Manual testing is time-consuming. Hiring experts to perform the tests is expensive. Furthermore, the test results cannot be retrieved and analyzed at a later time.

Accordingly, it is desired to develop a method for determining the dispersibility grade of a particulate material that will reduce discrepancies, reduce consumption of time, eliminate the need for experts, and allow retrieval and analysis of samples at a later time. It would also be desirable to develop a method for determining the dispersibility grade of a particulate material that can be performed at a location remote from the sample. It would also be desirable to develop a method for determining the dispersibility grade of a particulate material, which grade can be transmitted electronically as it is being determined.

Automated vision systems have been described in the art. See, for example, Gregory, "Planning a PC-Based Machine Vision System", SENSORS, April 1998, pages 12–18 and Claude and Carritte, "Increasing product Yields with Automated Vision Systems", Medical Device & Diagnostic Industry, May 2000, pages 158–169, both of which are incorporated herein by reference. However, the art has not addressed the problem of classifying the dispersiblity of particulate material according to a plurality of grade levels. The prior art is primarily concerned with a pass/fail decision and does not indicate a means for assigning samples into different categories.

SUMMARY OF THE INVENTION

This invention provides a method and apparatus for determining the dispersibility grade of particulate material by means of an image processing technique that employs machine vision.

In one aspect, this invention provides a method for grading the dispersibility of particulate material, the method comprising the steps of:

(a) obtaining an image, in digitized form, of a sample comprising reconstituted particulate material;

(b) performing a series of image processing steps to determine the presence and magnitude of blobs;

(c) performing a blob analysis to obtain data relating to the distribution of the particulate material in the sample;

(d) comparing the result of the blob analysis with data in a database; and (e) determining the grade of said particulate material by means of the comparison.

The sample of particulate material, which is typically in the form of a powder, is reconstituted preferably by means of agitating a container filled with the sample. The series of image processing steps preferably includes, but is not limited to the following: identifying the location of the particulate material; assigning grey-scale values to individual pixels that form the image; determining which pixels, by connecting to one another have formed into blobs; and reducing noise. As used herein, the term "pixel" means a picture element in an array of cells that form an image.

The database suitable for use in this invention can be established by recording the results of a large number of tests performed by a powder quality grading authority. As used herein, a "powder quality grading authority" is a person in an organization having the authority to determine grades of quality of a particulate material. The recorded test results are analyzed by one or more statistical methods, whereby they are classified according to grade levels. The grade levels are associated with several ranges that have emerged from the statistical analysis. For example, the ranges can be characterized by measures of central tendency, that is, the moments of a distribution, the median, and mode. In running a test, a digitized image of a sample of particulate material is made as the material is residing on the surface of a screen. A plurality of physical properties of the sample of the particulate material can be recorded and stored in a database. Statistical analyses can be performed to assign a grade level to the particulate material. Such analyses involve comparing the physical properties of the sample of particulate material with the data in the database.

In another aspect, this invention provides an apparatus suitable for grading the dispersibility of particulate material. The apparatus comprises:

(a) a sample holder;

(b) a source of light having a specified frequency band;

(c) a bandpass filter;

(d) a camera, preferably a CCD camera;

(e) a frame grabber; and (e) a computer.

The apparatus is typically commanded and controlled by software. In an alternative embodiment, the frame grabber can be incorporated into the camera, in which case, the camera and the frame grabber will be an integrated unit.

The method of this invention eliminates the need for human involvement in analyzing images, eliminates environmental influences (e.g., extraneous light), and eliminates subjective physical comparison. Accordingly, this invention eliminates human bias. The digitized images of samples and statistical results are retrievable for later analysis and future applications. The system can be used to provide standardized test results at a single production site or at a plurality of production sites. In addition, the test results can be transmitted to remote locations by means of computer networks, thereby allowing production decisions to be made rapidly.

DETAILED DESCRIPTION

As used herein, the term "dispersibility" means a degree of firmness and solubility of particulate material within a product. As stated previously, particulate material includes, but is not limited to, gel, mineral, oil. The term "grade" means a position in a scale of quality. The term "reconstituted" means to convert from a solid to a dispersion, suspension, or solution. The term "digitize" means assign to each pixel of an image a grey-scale value according to the brightness of the pixel. In this invention, grey-scale values of from 0 to 255 are adequate for digitizing an image. The expression "reference image" means a typical image that illustrates a particular grade. The expression "blob analysis" means a method of analyzing an image of a sample, which method is suitable for characterizing the brightness, shape, size, and other properties of particulate material in the sample. The expression "statistical analysis" typically refers to the analysis of measures of central tendency, also known as the moments of a distribution, the median, and mode. When a set of values has a sufficiently strong central tendency, that is, a tendency to cluster around some particular value, then it may be useful to characterize the set by a few numbers that are relate to its moments, which are the sums of integer powers of the values. Example of moments include, but are not limited to, mean, variance, standard deviation, average deviation, mean absolute deviation, skewness, and kurtosis. The term "database" means a group of data obtained by means of statistical analysis of numerous images, typically hundreds of images, divisible into a plurality of grade levels, typically six grade levels. The database contains ranges of mean, standard deviation, maximum particle size, and other relevant parameters, which ranges correspond to grade levels. The expression "window comparison" refers to a method of comparison in which a specified range of data is compared with the results of a test run. If the results of the test run fall within the range, the results are said to be within the window. The decision to accept or reject a product is based upon the determination that the results are inside of the window or outside of the window.

This invention provides a method for grading the dispersibility of particulate material, the method comprising the steps of:
(a) obtaining an image, in digitized form, of a sample comprising reconstituted particulate material;
(b) performing a series of image processing steps to determine the presence and magnitude of blobs;
(c) performing a blob analysis to obtain data relating to the distribution of the particulate material in the sample;
(d) comparing the result of the blob analysis with data in a database; and
(e) determining the grade of said particulate material by means of the comparison.

The sample of particulate material, which is typically in the form of a powder, is reconstituted preferably by means of agitating a container filled with the sample. The series of image processing steps preferably includes, but is not limited to the following: identifying the location of the particulate material; assigning grey-scale values to individual pixels that form the image; determining which pixels, by connecting to one another have formed into blobs; and reducing noise.

In order to carry out the method of this invention, a database must be prepared. The database comprises statistical data derived from the analyses of numerous results of calibration runs that had been performed by a powder quality grading authority. The results of calibration runs had been analyzed by means of statistical methods, and grade levels were established to correspond to statistical windows (ranges). The calibration runs used to prepare the database included a large number of digitized images. The windows (i.e., ranges) used in the method are obtained from a statistical analysis of at least 200 samples for each grade. Preferably, more than 200 samples are used for each grade. Most preferably, at least 600 samples are used for each grade.

Figure 1A:
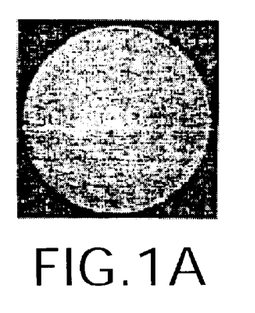
FIGS. 1A, 1B, 1C, 1D, 1E, and 1F constitute a series of digitized images illustrating typical grade levels associated with a dispersibility test.
Figure 1B:
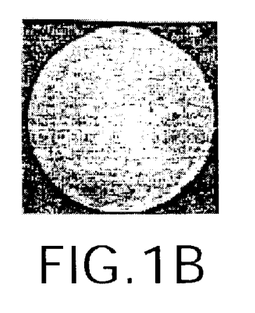
Figure 1C:
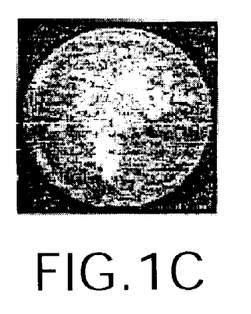
Figure 1D:
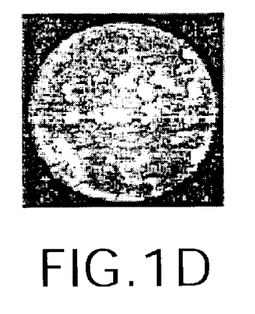
Figure 1E:
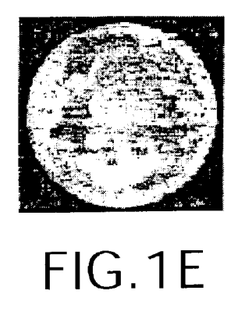
Figure 1F:
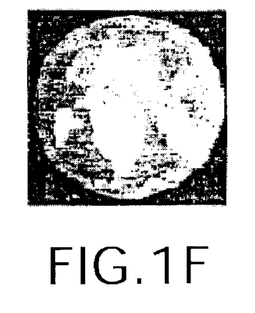

Each of the digitized images in the set of calibration runs represented a particular grade of particulate material. The use of statistical windows derived from a large number of digitized images makes it possible to describe the particulate material in terms of conventional parametric ranges. These conventional parametric ranges would have included, for example, number of particles per unit area, size range of particles, distribution of particles, maximum size of particles, and number of particles having a size greater than a specified size. The database can be stored in the memory of a computer. FIGS. 1A, 1B, 1C, 1D, 1E, and 1F, inclusive, illustrate digitized images of a type suitable for use in preparing the database of this invention. Each of the figures represents the mid-point of a given grade. FIG. 1A (Grade 1) illustrates an image where substantially no particulate material remains on the screen. FIG. 1F (Grade 6) illustrates an image where a significant quantity of particulate material remains on the screen. FIGS. 1B (Grade 2), 1C (Grade 3), 1D (Grade 4), and 1E (Grade 5) illustrate images where quantities of particulate material intermediate to the quantities shown in FIGS. 1A and 1F remain on the screen. It should be noted that the higher the grade number, the greater amount of particulate material remains on the screen.

The database of this invention is not a mere set of data. The database is an "expert system", which then takes the place of the powder quality grading authority. The development of an expert system may require a significant amount of time.

The database comprises data that take into account the following parameters: size of individual particles, shape of individual particles, location of individual particles, and distribution of populations of particles.

The method of this invention is able to distinguish foam from particulate material by means of processing techniques. Because foam obscures the particulate material, thereby making particulate material difficult to see and to identify, inexperienced operators find it difficult to classify dispersions of particulate material. This invention is designed to penetrate the bubbles on the surface of the foam and clear the shadow effect caused by the foam by means of spatial filtration and neighborhood comparison. These techniques are described in, for example, Davies, *Machine Vision: Theory, Algorithms, Practicalities*, 2nd Edition, Academic Press (1997), incorporated herein by reference. In particular, see pages 248–251 and 504–507 of Davies. The image obtained after image processing will be similar to the one obtained in the conventional method after acetone is sprayed over the foam to provide a clear view of the particulate material without breaking or denaturing proteinaceous material. In the conventional method, the acetone that is sprayed on the surface of the foam reduces the surface tension, with the result that a source of error is introduced into the grading process. Thus, the method of this invention eliminates a source of error and improves the effectiveness of the grading. More importantly, the method of this invention increases the accuracy of the grading by eliminating the possible breakdown or the denaturing of the coagulated particles of protein that occurs when procedures involving the spraying of acetone are utilized. The spraying of acetone on the surface of the sample tends to break the particulate material and produce false grade information, e.g., a sample having a low grade 3 may be classified as a sample having a high grade 2 after being sprayed with acetone.

Digitized images can be formed from as few as two digits, where, for example, the digit "1" represents white and the digit "0" represents black. Preferably, the digitized images are formed from eight bits, wherein grey-scale values range from 0 to 255, with, for example, "0" being black and "255" being white. In other words, for each pixel in the image, the light reflected is assigned a value of from 0 to 255, the value corresponding to brightness, with "0" being the darkest (minimum reflection) and "255" being the brightest (maximum reflection). The grey-scale values are based on reflection images of solid material that was retained on a screen, e.g., an 80-mesh screen in the case of grading for dispersibility of infant formula powder.

Figure 2A:
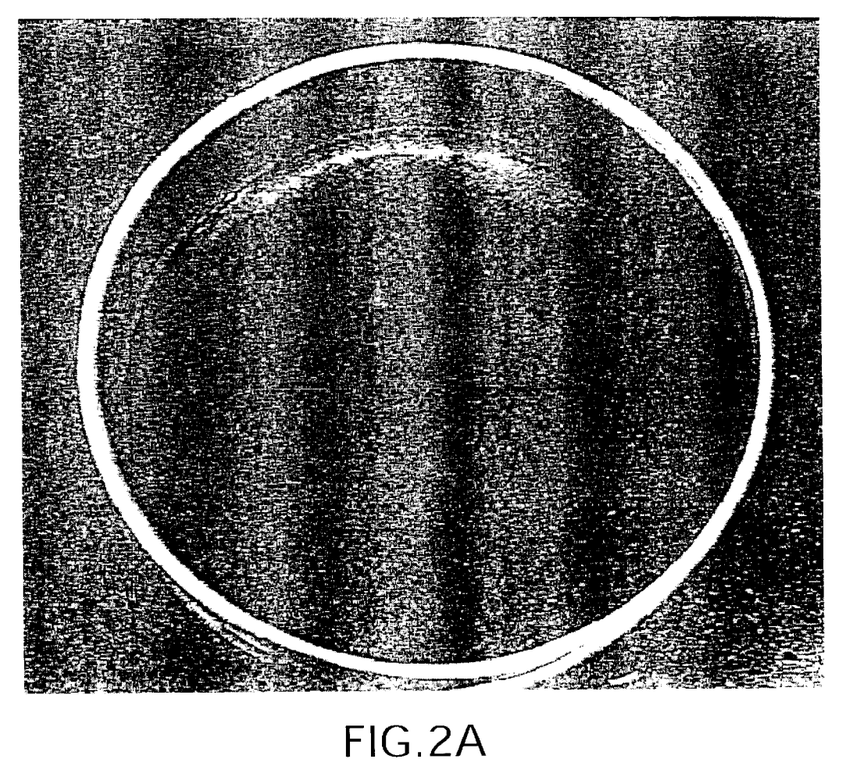
FIGS. 2A, 2B, 2C, 2D, 2E, and 2F constitute a series of reference images illustrating typical grade levels associated with a dispersibility test.
Figure 2B:
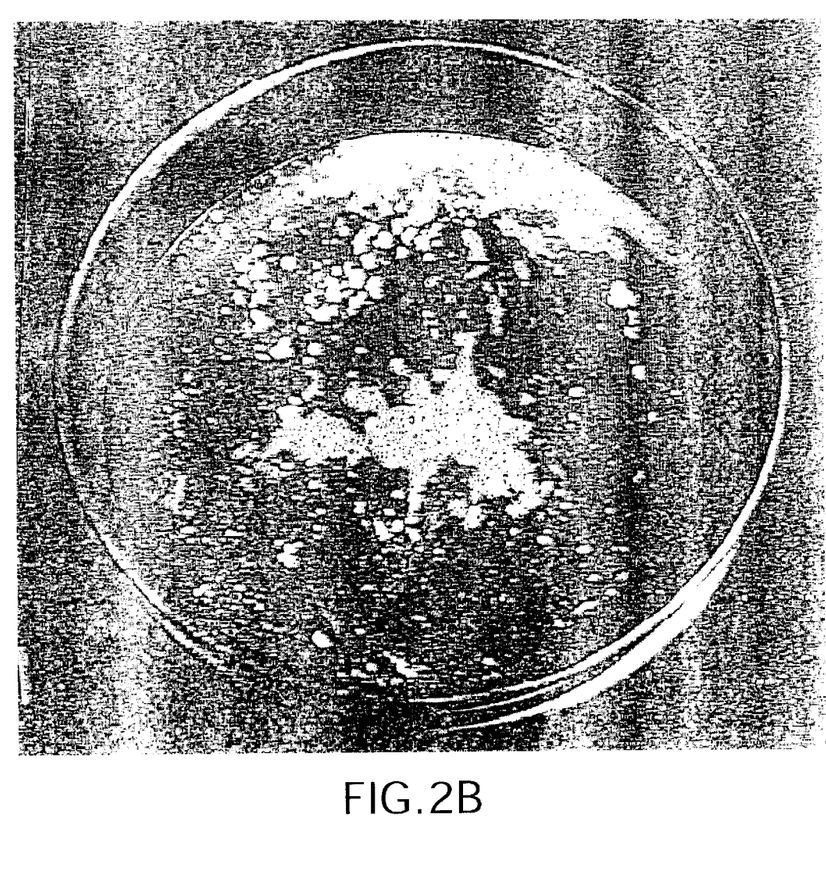
Figure 2C:
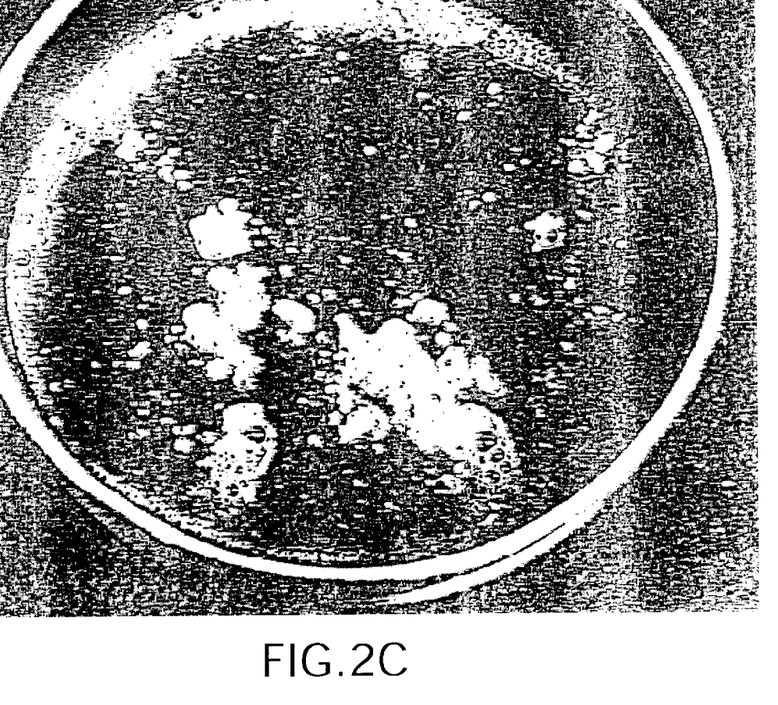
Figure 2D:
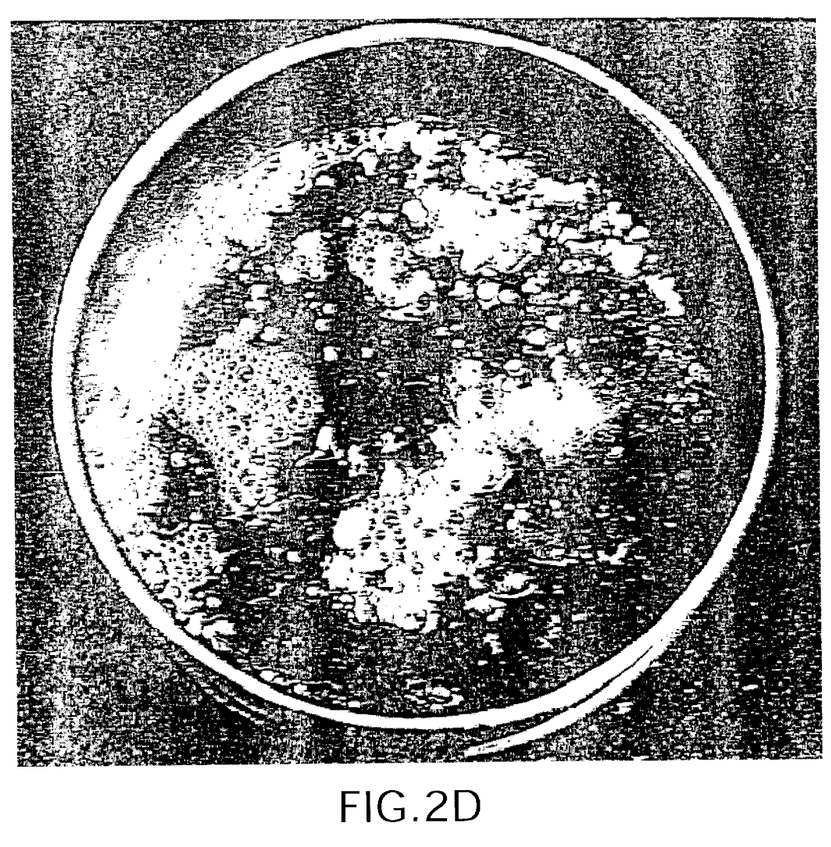
Figure 2E:
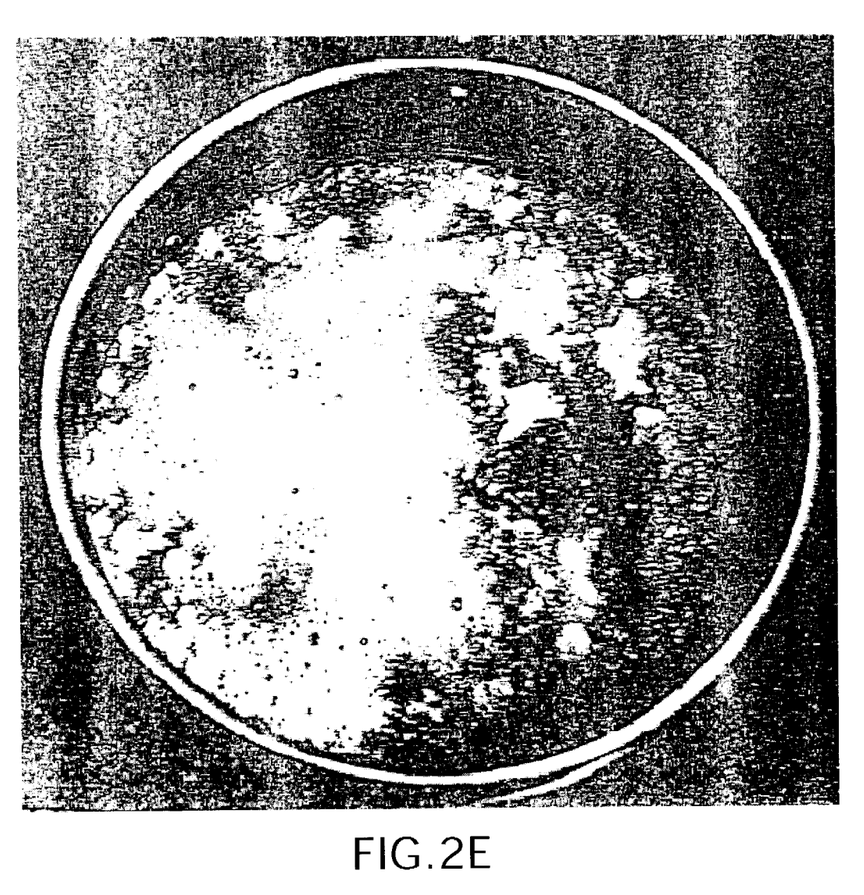
Figure 2F:
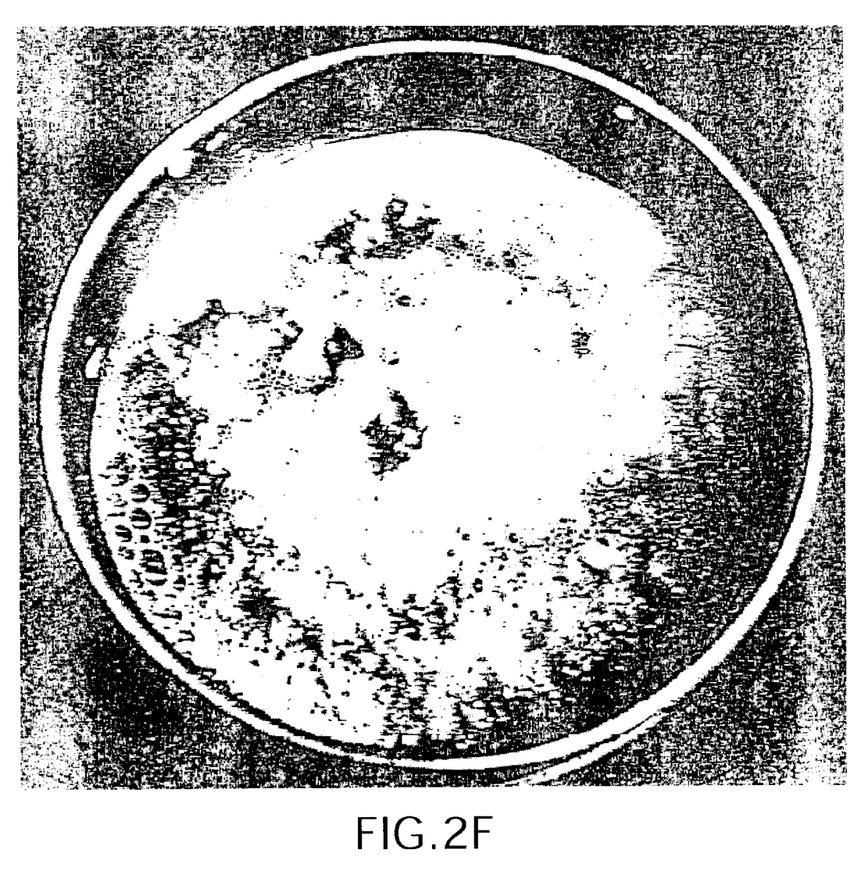

Reference images representing a plurality of grades of samples are used for visual comparison during the process of calibrating the apparatus for carrying out the method of this invention. The actual reference images have no effect on decision making with respect to grading samples or establishing a database. FIGS. 2A, 2B, 2C, 2D, 2E, and 2F show reference images that are used by a powder quality grading authority for grading dispersibility of powder. FIG. 2A shows a sample having a grade of 1; FIG. 2B shows a sample having a grade of 2; FIG. 2C shows a sample having a grade of 3; FIG. 2D shows a sample having a grade of 4; FIG. 2E shows a sample having a grade of 5; FIG. 2F shows a sample having a grade of 6. The benefit of this invention is that an evaluator of samples will not be required to search for individual reference images during the grading process, as is required in the conventional method.

Figure 3:
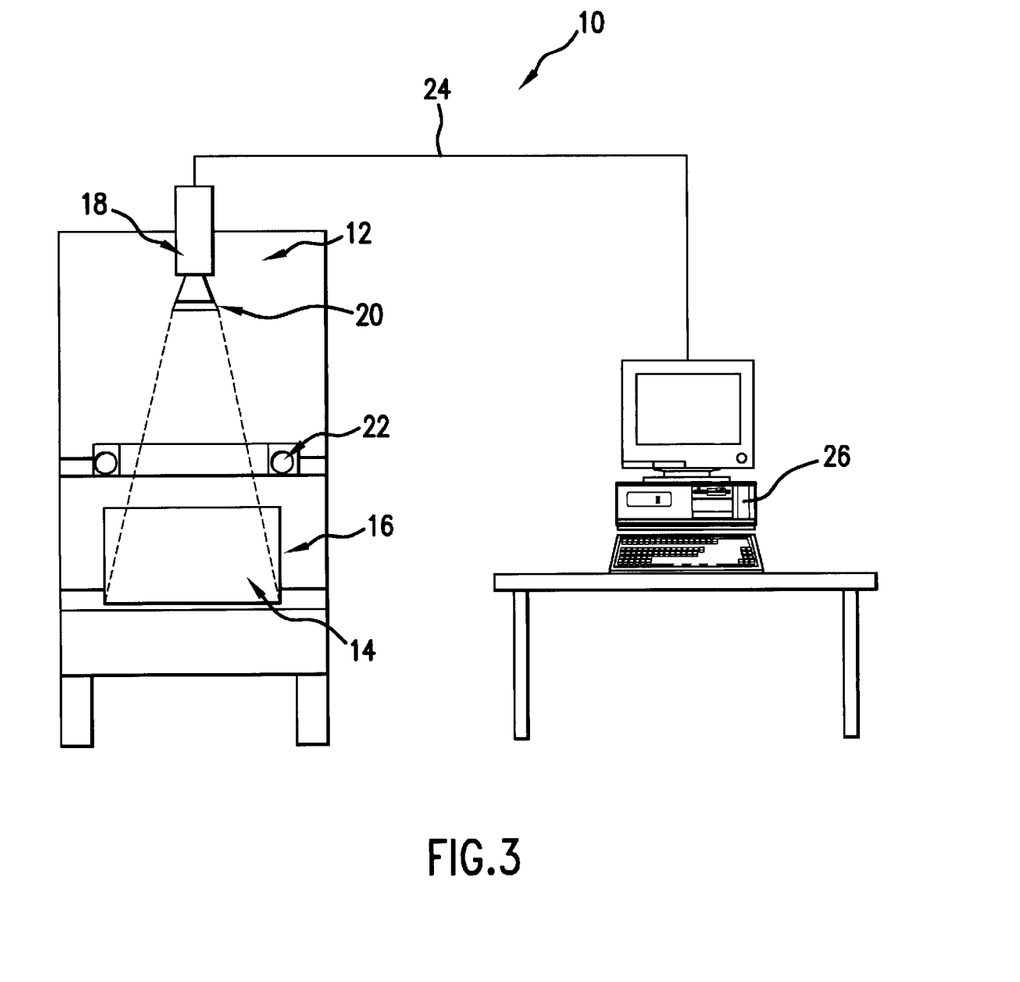
FIG. 3 is a schematic diagram of apparatus suitable for carrying out the method of this invention.
Figure 4:
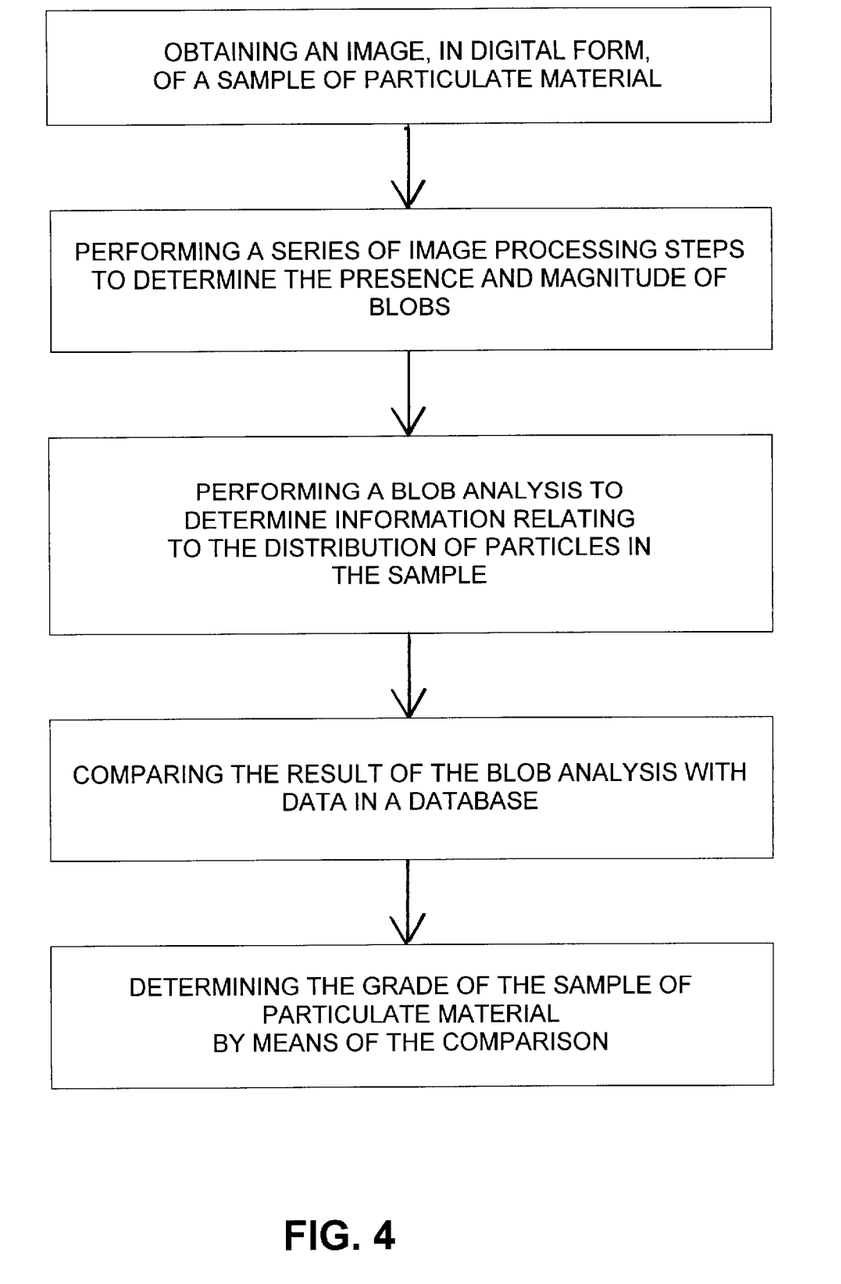
FIG. 4 is a flow chart illustrating the steps of the method of this invention.
Figure 5:
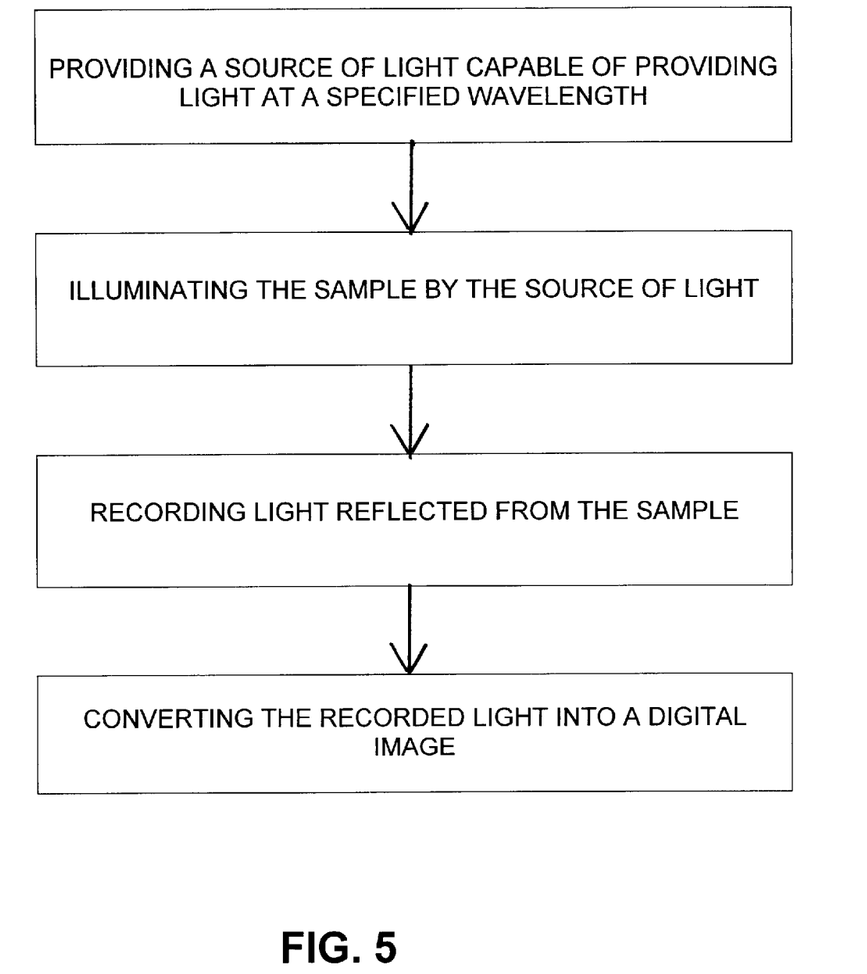
FIG. 5 is a flow chart illustrating the steps of this invention for preparing a digitized image.

Referring now to FIG. 3, the apparatus 10 comprises a test chamber 12 in which is placed a sample 14 on a screen 16, preferably an 80-mesh screen. A CCD camera 18 is focused on the sample 14 on the screen 16. If required, i.e., if the camera does not have a frame grabber incorporated therein, a frame grabber (not shown) can also be included in the apparatus. The purpose of the frame grabber is to convert an analog image from the camera and convert it into digital information for use by the computer. A bandpass filter 20 is placed between the CCD camera 18 and a source of light 22, preferably visible light. The source of light 22 is disposed between the bandpass filter 20 and the sample 14 on the screen 16. A cable 24 connects the CCD camera 18 to a computer 26. The functions of these components are described in Gregory, "Planning a PC-Based Machine Vision System", SENSORS, April 1998, pages 12–18, Claude and Carritte, "Increasing product Yields with Automated Vision Systems", Medical Device & Diagnostic Industry, May 2000, pages 158–169, and Davies, Machine Vision: Theory, Algorithms, Practicalities, 2nd Edition, Academic Press (1997), all of which were previously incorporated herein by reference.

These components are commercially available; suitable commercially available components include the following:
 (a) "Epix PixCI" PCI Frame Grabber
 (b) PDB15-2-BNCP Digital I/O Cable
 (c) RL 1660 LED "Apposolite", 660 nm wavelength, 35–70 mm field of view, Advanced Illumination Inc., 24 Peavine Drive, Rochester, Vt. 05767 (light source)
 (d) Bandpass Filter (to ensure that only the light intensity of the system will be detected by the camera and that the light passing through the filter will be primarily of the desired wavelength)
 (e) "Pulnix" TM-200 High resolution CCD camera, Pulnix America Inc. 1330 Orleans Dr. Sunnyvale, Calif. 94089
 (f) "Fujinon" CCTV Lens HF9A-2, Fujinon Inc., 10 High Point Dr. Wayne, N.J. 07470
 (g) "AST" 133 Mhz computer The apparatus employs a light source having a specified frequency band and a filter corresponding to that frequency band applied to the camera, thereby ensuring that the surrounding light will only minimally interfere with the calibrations runs and grading runs.

In order to provide a grade of dispersibility for a sample 14 of particulate material, an image must be made of a sample 14 of the particulate material. A mixture containing the sample 14 of the particulate material in a liquid carrier is applied to a screen 16 (Market Grade Sieve, Mesh 80, Dual MFG Co. Chicago, Ill. 60618). The 80-mesh screen is preferred because this screen size best replicates the nipple size opening, thereby indicating the risk of nipple clogging as well as solubility of particles, sediment, and creaming.

The source of light 22 can generate light of a specific intensity at a certain wavelength so that the light can pass the bandpass filter 20, thereby assuring that the illumination intensity on the sample 14 is constant.

The image of the sample 14 can be made by a CCD camera 18, which records the image in digitized form, so that conversion of the image from analogue format to digital format is not required.

A series of image processing steps is employed to provide an image that is suitable for analysis. An image processing method that is suitable for use in this invention is thresholding. In the thresholding technique, a grey-scale image is converted to a binary image. For example, in a grey-scale image wherein the pixels have a value of from 0 to 255, inclusive, all pixels having a brightness above a certain threshold value (e.g., 180) are converted to 255 and all pixels having a brightness below that threshold value (e.g., 180) are converted to 0. This manner of conversion simplifies procedures in the latter stages of image processing and reduces the time of image processing. Image processing techniques suitable for use in this invention are known to one having ordinary skill in the art of image processing. For further information on thresholding, see Davies, *Machine Vision: Theory, Algorithms, Practicalities*, 2nd Edition, Academic Press (1997), previously incorporated herein by reference. In particular, see pages 79–101 of Davies. Other types of image processing techniques and the component steps thereof are shown in Davies, *Machine Vision: Theory, Algorithms, Practicalities*, 2nd Edition, Academic Press (1997).

The next step in the method involves performance of a blob analysis to determine the appropriate grade of the sample. This step is important because blobs are highly determinative of the grade to be assigned to a sample. Most machine vision protocols attempt to determine the number of defects and locate their position. In a blob analysis, the machine vision protocol attempts to determine the size, shape, and location of particulate material, because the size, shape, and location of particulate material are critical to a determination of the quality of the product. In other words, the statistical information with respect to a blob or blobs determines the quality of the product.

Blob analysis is one of the most important steps in the method of this invention. Blob analysis provides information relating to at least one of the following parameters:

(a) the number of pixels in the region encompassed by the blob;

(b) the area of the region encompassed by the blob;

(c) the two points on the boundary of the region encompassed by the blob that define the major axis of the blob;

(d) the two points on the boundary of the region encompassed by the blob that define the minor axis of the blob;

(e) the length of the major axis of the region encompassed by the blob;

(f) the angle of the major axis of the region encompassed by the blob, (g) the distance of the minor axis from the major axis in the region encompassed by the blob;

(h) the circumference of the region encompassed by the blob (the sum of the distances from pixel to pixel around the boundary of the region);

(i) the center of mass of the region encompassed by the blob;

(j) the point (pixel) that defines the minimum radius from the center of mass of the region encompassed by the blob;

(k) the point (pixel) that defines the maximum radius from the center of mass of the region encompassed by the blob;

(l) the distance of the minimum radius from center of mass of the region encompassed by the blob, (m) the distance of the maximum radius from center of mass of the region encompassed by the blob;

(n) four points on the boundary of the region encompassed by the blob, which points are the minimum horizontal coordinate, the maximum horizontal coordinate, the minimum vertical coordinate, and the maximum vertical coordinate;

(o) the width of the region encompassed by the blob as projected on the horizontal axis;

(p) the height of the region encompassed by the blob as projected on the vertical axis;

(q) the angle of the line of least moment of inertia.

As used herein, the two points that define the major axis are farther apart than any other pair of points, with respect to horizontal and vertical coordinates. The two points on the boundary of the region encompassed by the blob that define the minor axis, together with the points that delineate the major axis, define a rectangle enclosing the region encompassed by the blob. These parameters are described in greater detail in Reference Manual, PXIPL Image Processing "C" Library, Version 2.5 (1997) (EPIX, Inc., 381 Lexington Dr., Buffalo Grove, Ill. 60089), incorporated herein by reference. If desired, additional information can be recorded. After the forgoing information on the sample is obtained, a statistical analysis is conducted to categorize the sample. Blob analysis is further described in Davies, *Machine Vision: Theory, Algorithms Practicalities*, 2nd Edition, Academic Press (1997), previously incorporated herein by reference. In particular, see pages 347–370 of Davies.

The statistical information obtained from a blob analysis of a digitized image can then be compared to statistical information in the database. By means of this comparison, the particulate material in the sample can be assigned a grade. The following table (Table 1) indicates parameters that can be used to classify digitized images into various grades. It should be noted that additional parameters can be and often are used.

TABLE 1

| Grade | Mean particle size (pixels) | Largest particle size (pixels) | Skewness |
|---|---|---|---|
| 1 | $0 \leq 25$ | $\leq 80$ | <3 |
| 2 | $25 \leq 125$ | $>80 \leq 2000$ | <3 |
| 3 | $125 \leq 225$ | $>2000 \leq 6500$ | <3 |
| 4 | $225 \leq 325$ | $>6500 \leq 16000$ | <3 |
| 5 | $325 \leq 525$ | $>16000 \leq 28000$ | <3 |
| 6 | $>525$ | $>28000$ | $\geq 3$ |

Validation is a process for challenging a developed standard with extreme and frequent cases in the range encompassed by the standard to prove that the standard is valid in the specified range. In a validation operation, the statistical parameters obtained from the digitized image will be compared with the statistical parameters of the database. The validated database consists of several grade windows. As long as each result can be allocated to a specific grade window, the grade value will be reliable. There are also two extremes to cover the situation of no sample at all and an abnormal sample. In these extremes, the system will provide a warning and no grade will be given. So long as the data falls into a window corresponding to one of the grades, valid information relating to the grade of the sample will be provided. Experts who have established the grades for each of the windows are typically well-trained authorities, internal to the organization, who have developed and validated the grading method, which has been accepted by the internal quality assurance function and the appropriate governmental agency.

The following procedure is used to calibrate the apparatus 10:

1. Power for computer 26 is switched on and a red light (wavelength=660 nm) inside the test chamber 12 is switched on. The switch for the red light is located at the bottom of the test chamber 12. The intensity setting of the display is 100.

2. The computer program is then begun.
3. In the computer program, the file saving dialog box is opened. The name of a file is specified. In a typical program, the name of the file has a suffix "txt" (for example, a typical file name is "aa.txt"). The file, which only needs to be specified once, will retain all statistical data for the test. If the name of the file provided already exists, the computer will indicate that fact. Then another name of a file will have to be specified. Images will be saved with the same name as the file but with a different suffix automatically. A typical suffix for an image is "bmp".
4. The name of the file is then confirmed.
5. The mesh screen 16 and the sample 14 supported thereon are inserted into the test chamber 12 at the proper position therein. Foaming of the sample 14 should be reduced to a minimum level before the calibration run is begun.
6. The image of the sample 14 is adjusted, if necessary, until it appears on the screen of the computer 26.
7. The calibration program is then begun.
8. The grade level is selected in accordance with the result recorded by the powder quality grading authority. The grade is then confirmed.
9. Steps 5 through 8 are repeated until the run is completed or the operator closes the program.

A sufficient number of calibration runs must be performed for each grade in order to create a statistically significant database or expert system. Accordingly, it is preferred that at least 200 samples graded by a powder quality grading authority be input to the database for each grade. Thus, if the database is to have, for example, six grade windows, it is preferred that 1200 samples, 200 samples for each grade, be input to calibrate the expert system. It should be noted that the calibration procedure involves an interaction between the powder quality grading authority, i.e., a human being, and the computer (see step 8).

The following procedure is used to grade a sample of particulate material with the apparatus:

1. Power for computer 26 is switched on and a red light (wavelength=660 nm) inside the test chamber 12 is switched on. The switch for the red light is located at the bottom of the test chamber 12. The intensity setting of the display is 100.
2. The computer program is then begun.
3. In the computer program, the file saving dialog box is opened. The name of a file is specified. In a typical program, the name of the file has a suffix "txt" (for example, a typical file name is "aa.txt"). The file, which only needs to be specified once, will retain all statistical data for the test. If the name of the file provided already exists, the computer will indicate that fact. Then another name of a file will have to be specified. Images will be saved with the same name as the file but with a different suffix automatically. A typical suffix for an image is "bmp".
4. The name of the file is then confirmed.
5. The mesh screen 16 and the sample 14 supported thereon are inserted into the test chamber 12 at the proper position therein. Foaming of the sample 14 should be reduced to a minimum level before the grading run is begun.
6. The image of the sample 14 is adjusted, if necessary, until it appears on the screen of the computer 26.
7. The grading program is then begun.
8. The grade level of the sample is determined by the program after the program compares the statistical data derived from the digitized image of the sample with the data in the database.
9. The grade level is then confirmed.
10. Steps 5 through 9 are repeated until the test is completed or the operator closes the program.

The program can then be exited. In the grading run, the computer via a program compares the statistical information obtained by means of image processing and statistical analysis of the processed image of the sample with the data in the database to determine into which grade window the sample should be classified. In the grading run, there is no interaction between a human being and the computer in step 8.

The data used in calibration runs and grading runs and the results of calibration runs and grading runs can be stored in locations remote from the location of samples. Transmission of data and results can be performed by electronic means, such as, for example electronic mail and the internet. There are numerous benefits resulting from remote storage and transmission of data and results. One major benefit is uniformity or consistency of grading. Substantially similar samples will have the same grade no matter where they are examined. Another major benefit is rapidity in grading. In most cases, the computer by means of the database can reach a grading decision more rapidly than can a human powder grading authority. A third major benefit is accuracy. The use of image processing techniques to distinguish foam from particulate material eliminates the need for spraying the sample with acetone, hence avoiding the breakdown of particulate material and denaturing of proteinaceous material, thereby eliminating a major source of error. A fourth major benefit is the capability for the system to allow an operator to make decisions regarding the product in real time at a remote location. For example, a production line may be producing product containing particulate material having an unacceptable grade, as determined by the method of this invention. A quality assurance manager, at a location remote from the production line, can be provided an image via internet or electronic mail to facilitate decision-making. Process parameters can be adjusted after the source of the deviation is identified, thereby preventing loss of the batch. Under conventional operating conditions, the local powder quality grading authority would have to make the determination of the grade visually and then orally describe the facts to the appropriate quality assurance manager for a decision to be made. Only upon receipt of the oral description of the product would the quality assurance manager have the opportunity to give an order to modify the process parameters on the production line. This feature could ultimately result in tremendous cost savings to the production facility.

The evaluations performed by the method of this invention are able to more accurately predict the performance of a product with respect to passing through the opening of a nipple. This invention involves an expert system for determining the dispersibility of particulate material, in particular infant powder, rather than the mere use of machine vision and statistical analysis. The expert system provides accuracy, reliability, and efficiency in grading samples with respect to the degree of particulate material therein.

The following non-limiting example further illustrates the present invention.

EXAMPLE 1

In order to illustrate the invention, an example will be provided. Preparation of a sample requires the following equipment:

(a) 8 oz glass bottle (Ross commodity 04032) (the 8 oz glass bottle is used to simulate the ready-to-feed, reconstituted sample in a bottle)

(b) Bottle cap (Ross commodity 17871)

(c) Balance (Mettler PC 4400 or equivalent)

(d) Screen, 80-mesh U.S. standard sieve, 5 inch diameter (e) Mechanical shaker (Ross Model No. 1)

(f) General laboratory thermometer

Preparation of a sample requires the following steps:

(a) weigh, in duplicate, the correct amount of particulate material (powder) for each sample to be tested;

(b) add tap water (180 mL) at the correct temperature (±5°) into an 8 oz. Bottle;

(c) add the weighed sample to the surface of the water and place the cap on the bottle (duplicate samples may be prepared and shaken at the same time)

(d) immediately place the bottle into the mechanical shaker sample tray, making sure that the sample rods in the sample tray are in the upper position;

(e) remove any rods that are not being used;

(f) close the lid, latch it securely, and then close the safety shield lid;

(g) set the speed control dial at 4 cycles per second and the timer at 10 seconds, and then push the start button; the shaker will automatically stop when the timer stops;

(f) remove the bottle from the mechanical shaker and immediately pour the reconstituted product through an 80-mesh screen;

(g) fill the bottle approximately one-quarter full with tap water to dislodge any particles that may remain in the bottle, and pour through the screen;

(h) rate the particles remaining on the screen by means of the method of this invention;

(i) each sample should be tested in duplicate and the average reported as the final result.

The motion of the shaker is very violent under normal operating conditions. It is important to move any rods that do not have samples on them before shaking. Rods that do not have samples on them may eject out of their resting place in the sample tray and cause damage to the shaker and/or bodily harm.

Apparatus of the type shown in FIG. 3 can be used to grade the particulate material in the sample.

The following table (Table 2) shows the output of a grading run, which comprises data obtained from the statistical analysis of digitized images of samples.

Various modifications and alterations of this invention will become apparent to skilled in the art without departing from the scope and spirit of this invention, and it should be understood that this invention is not to be unduly limited to the illustrative embodiments set forth herein.

What is claimed is:

1. A method for grading the dispersibility of particulate material, said method comprising the steps of:

(a) obtaining an image, in digital form, of a sample of particulate material, wherein said sample of particulate material contains foam;

(b) performing a series of image processing steps to determine the presence and magnitude of blobs;

(c) performing a blob analysis to determine information relating to the distribution of particles in said sample;

(d) comparing the result of said blob analysis with data in a database; and (e) determining the grade of said sample of particulate material by means of said comparison, wherein said particulate material is not denatured during said method.

2. The method of claim 1, wherein image of said sample of said particulate material is prepared when said sample has been applied to a screen.

3. The method of claim 1, wherein said blob analysis involves measurement of at least one of the following parameters:

(a) the number of pixels in the region encompassed by the blob;

(b) the area of the region encompassed by the blob;

(c) the two points on the boundary of the region encompassed by the blob that define the major axis of the blob;

(d) the two points on the boundary of the region encompassed by the blob that defines the minor axis of the blob;

(e) the length of the major axis of the region encompassed by the blob;

(f) the angle of the major axis of the region encompassed by the blob, (g) the distance of the minor axis from the major axis in the region encompassed by the blob;

(h) the circumference of the region encompassed by the blob (the sum of the distances from pixel to pixel around the boundary of the region);

(i) the center of mass of the region encompassed by the blob;

(j) the point (pixel) that defines the minimum radius from the center of mass of the region encompassed by the blob;

TABLE 2

| Sample no. | Mean particle size | Maximum particle size | Standard Deviation | Skewness | Number of particles | Grade | Filename |
|---|---|---|---|---|---|---|---|
| 1 | 8.81 | 37 | 10.6 | 1.29 | 16 | 1 | Szzz.bmp |
| 2 | 9.09 | 154 | 25.68 | 4.36 | 46 | 2 | Szzz1.bmp |
| 3 | 40.07 | 2370 | 183.44 | 9.82 | 302 | 3 | Szzz2.bmp |
| 4 | 20.28 | 506 | 57.77 | 6.4 | 100 | 2 | Szzz3.bmp |
| 5 | 33.14 | 532 | 71.99 | 4.13 | 212 | 3 | Szzz4.bmp |
| 6 | 75.38 | 4652 | 359.44 | 10.15 | 217 | 3 | Szzz5.bmp |
| 7 | 27.17 | 337 | 63.59 | 3.31 | 60 | 2 | Szzz6.bmp |
| 8 | 76.02 | 1223 | 217.07 | 4.05 | 47 | 2 | Szzz7.bmp |
| 9 | 40.39 | 645 | 95.38 | 4.24 | 71 | 2 | Szzz8.bmp |
| 10 | 49.46 | 6882 | 144.95 | 4.06 | 65 | 4 | Szzz9.bmp |

(k) the point (pixel) that defines the maximum radius from the center of mass of the region encompassed by the blob;

(l) the distance of the minimum radius from center of mass of the region encompassed by the blob, (m) the distance of the maximum radius from center of mass of the region encompassed by the blob;

(n) four points on the boundary of the region encompassed by the blob, which points are the minimum horizontal coordinate, the maximum horizontal coordinate, the minimum vertical coordinate, and the maximum vertical coordinate;

(o) the width of the region encompassed by the blob as projected on the horizontal axis;

(p) the height of the region encompassed by the blob as projected on the vertical axis;

(q) the angle of the line of least moment of inertia.

4. The method of claim 1, wherein said data in said database comprises statistical data that relates to at least one of the following parameters: size of individual particles of particulate material, shape of individual particles of particulate material, location of individual particles of particulate material, and distribution of populations of particles of particulate material.

5. The method of claim 1, wherein said database comprises a plurality of windows for determining the grade of said particulate material.

6. The method of claim 1, wherein said image is transmitted to a location remote from said sample by electronic means.

7. The method of claim 1, wherein said data is transmitted to a location remote from said sample by electronic means.

8. The method of claim 1, wherein said grade determination is transmitted to a location remote from said sample by electronic means.

9. The method of claim 1, wherein said data is stored at a location remote from said sample by electronic means.

10. The method of claim 1, wherein said digitized image is prepared by
  (a) providing a source of light capable of providing light at a specified wavelength;
  (b) illuminating said sample by said source of light;
  (c) recording light reflected from said sample; and
  (d) converting said recorded light into a digital image.

11. The method of claim 1, wherein said database comprises statistical data derived from the analyses of a plurality of results of calibration runs that had been performed by a powder quality grading authority.

12. The method of claim 11, wherein said results of said calibration runs had been analyzed by means of statistical methods.

13. The method of claim 12, wherein said grade levels were established to correspond to statistical windows (ranges).

14. The method of claim 13, wherein said windows (ranges) used in said method are obtained from a statistical analysis of at least 200 samples for each grade.

15. An apparatus for determining the grade of a sample comprising particulate material, said apparatus comprising:
  (a) a sample holder for holding a sample of particulate material on a screen, said sample of particulate material containing foam;
  (b) a source of light for illuminating said sample on said screen;
  (c) a bandpass filter;
  (d) means for preparing a digitized image of the distribution of particles in said particulate material; and
  (e) a computer for comparing statistical information obtained by means of a statistical analysis of said digitized image to a database comprising ranges that represent grade levels.

16. The apparatus of claim 15, wherein said screen is an 80-mesh screen.

17. The apparatus of claim 15, wherein said source of light provides visible light.

* * * * *